United States Patent
Gordon et al.

(10) Patent No.: US 7,644,603 B2
(45) Date of Patent: Jan. 12, 2010

(54) METHOD OF TESTING A SURGICAL SYSTEM

(75) Inventors: Raphael Gordon, San Dimas, CA (US); Michael D. Morgan, Costa Mesa, CA (US)

(73) Assignee: Alcon, Inc., Hunenburg (CH)

( * ) Notice: Subject to any disclaimer, the term of this patent is extended or adjusted under 35 U.S.C. 154(b) by 662 days.

(21) Appl. No.: 11/167,646

(22) Filed: Jun. 27, 2005

(65) Prior Publication Data

US 2008/0006096 A1 Jan. 10, 2008

(51) Int. Cl.
*G01L 27/00* (2006.01)
(52) U.S. Cl. ....................... 73/1.57; 73/865.9
(58) Field of Classification Search ........... 422/99, 422/100; 141/94, 98; 73/1.57, 37, 865.9
See application file for complete search history.

(56) References Cited

U.S. PATENT DOCUMENTS

| | | | |
|---|---|---|---|
| 3,589,363 A | 6/1971 | Banko et at | |
| 4,041,947 A | 8/1977 | Weiss et al. | |
| 4,223,676 A | 9/1980 | Wuchinich et al. | |
| 4,246,902 A | 1/1981 | Martinez | |
| 4,493,694 A | 1/1985 | Wuchinich | |
| 4,515,583 A | 5/1985 | Sorich | |
| 4,548,205 A | 10/1985 | Armeniades et al. | |
| 4,589,415 A | 5/1986 | Haaga | |
| 4,609,368 A | 9/1986 | Dotson, Jr. | |
| 4,722,350 A | 2/1988 | Armeniades et al. | |
| 4,841,984 A | 6/1989 | Armeniades et al. | |
| 4,869,715 A | 9/1989 | Sherburne | |
| 4,922,902 A | 5/1990 | Wuchinich et al. | |
| 4,989,583 A | 2/1991 | Hood | |
| 4,998,914 A | 3/1991 | Wiest et al. | |
| 5,154,694 A | 10/1992 | Kelman | |
| 5,267,956 A | 12/1993 | Beuchat et al. | |
| 5,359,996 A | 11/1994 | Hood | |
| 5,364,342 A | 11/1994 | Beuchat et al. | |
| 5,494,530 A | 2/1996 | Graf | |
| 5,499,969 A | 3/1996 | Beuchat et al. | |
| 5,556,378 A | 9/1996 | Storz et al. | |
| 5,586,973 A | 12/1996 | LeMaire et al. | |
| 5,609,576 A | 3/1997 | Voss et al. | |
| 5,899,674 A | 5/1999 | Jung et al. | |
| 6,293,926 B1 | 9/2001 | Sorensen et al. | |
| 6,875,194 B2 * | 4/2005 | MacKool | 604/28 |
| 6,986,753 B2 | 1/2006 | Bui | |
| 2002/0019607 A1 | 2/2002 | Bui | |

(Continued)

OTHER PUBLICATIONS

Initial publication without International Search Report for PCT/US2006/023145, Publication No. WO2007/001859, 20 pages.

(Continued)

*Primary Examiner*—John Fitzgerald
(74) *Attorney, Agent, or Firm*—Russell Henrichs

(57) ABSTRACT

A method of testing a surgical system that takes advantage of the fact that in a balanced irrigation/aspiration system (inflow≧outflow) the duration of the aspiration pressure recovery to the irrigation fluid source pressure immediately following pump stop is independent of pump run time. This method provides a more reliable way of detecting restricted irrigation flow configurations not detectable by the current methods, such as marginal irrigation flow cases that could potentially lead to surgical complications (e.g. chamber collapse during post-occlusion break surge).

19 Claims, 5 Drawing Sheets

U.S. PATENT DOCUMENTS

| | | |
|---|---|---|
| 2003/0190244 A1 | 10/2003 | Davis et al. |
| 2004/0089080 A1* | 5/2004 | Kadziauskas et al. ...... 73/865.9 |
| 2004/0167462 A1* | 8/2004 | MacKool ...................... 604/27 |
| 2004/0187613 A1 | 9/2004 | Peacey et al. |
| 2005/0080375 A1* | 4/2005 | Kadziauskas et al. ......... 604/39 |
| 2006/0058811 A1 | 3/2006 | Kishimoto et al. |
| 2007/0010730 A1* | 1/2007 | Gordon ...................... 600/398 |
| 2008/0006096 A1* | 1/2008 | Gordon et al. ........... 73/861.43 |
| 2008/0033349 A1* | 2/2008 | Suzuki ........................ 604/35 |

OTHER PUBLICATIONS

Later publication of International Search Report for PCT/US2006/023145, Publication No. WO2007/001859, 2 pages.

Initial Publication without International Search Report for PCT/US2006/023656, Publication No. WO2007/001929, 12 pages.

Later Publication of International Search Report for PCT/US2006/023656, Publication No. WO2007/001929, 2 pages.

Supplementary European Search Report for Application No. EP 06 78 5059, Publication No. 1895958, 2 pages.

* cited by examiner

METHOD OF TESTING A SURGICAL SYSTEM

BACKGROUND OF THE INVENTION

This invention relates generally to the field of cataract surgery and more particularly to a surgical parameters control method for use with a phacoemulsification system.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye though the open end of the cutting tip, the cutting tip and horn bores and the aspiration line and into a collection device. The aspiration of emulsified tissue is aided by a saline flushing solution or irrigant that is injected into the surgical site though the small annular gap between the inside surface of the irrigating sleeve and the cutting tip.

Prior to use in surgery, the various handpieces, tubings and fluid management cassettes all need to be purged of air or primed. During the priming stage, current phacoemulsification systems also run an aspiration system diagnostic step to test for leaks or blockages in the aspiration system. During this diagnostic step, the system pump is activated to generate a certain vacuum in the aspiration line. If the system is not able to reach the desired vacuum level, this indicates to the system that there is a leak somewhere in the aspiration system, and the system will sound a warning for the operator. On the other hand, inability to release previously build vacuum indicates that there is a blockage in the system, such as a kink in one of the tubings.

Following the priming step, a flow check is performed specifically intended to verify an adequate fluid flow through the surgical handpiece. Current phacoemulsification systems use a small rubber test chamber that fits over the cutting tip and sleeve. The test chamber is filled with the irrigation fluid and when placed on the handpiece creates a closed compliant aspiration system. During this test an excessive vacuum level for a given pump speed would indicate a flow restriction in the fluidic path. Also, a manual check can be performed by the user to ensure that the test chamber is filled and pressurized upon test completion. A deflated test chamber would be an indication of the irrigation flow restriction.

While this priming and diagnostic system procedure is effective, it can cause some compromises with current phacoemulsification system technology. For example, phacoemulsification tip technology has evolved over the years and many different tip styles and diameters are now available. As will be understood to one skilled in the art, an aspirating tip with a small diameter or bore will naturally have a higher resistance to flow than a large bore tip. Therefore, at any given pump speed, a small bore tip will create a higher vacuum in the aspiration line than a large bore tip. As a result, diagnostic settings that use a vacuum level compatible with a small bore tip may not be appropriate when a large bore tip is used, and visa versa. This can lead to inaccuracies and false warnings by the system. Similar inaccuracies can result from different sized tubings and handpieces. Also, a reliance on the user to verify a proper test chamber state following the diagnostics completion is subjective and susceptible to a human error.

Therefore, a need continues to exist for a method of priming and testing phacoemulsification systems that is accurate for a wide variety of handpieces, tubings and tip.

BRIEF SUMMARY OF THE INVENTION

The present invention improves upon the prior art by providing a method of testing a surgical system that takes advantage of the fact that in a balanced irrigation/aspiration system (inflow≧outflow) the duration of the aspiration pressure recovery to the irrigation fluid source pressure immediately following pump stop is independent of pump run time. This method provides a more reliable way of detecting restricted irrigation flow configurations not detectable by the current methods, such as marginal irrigation flow cases that could potentially lead to surgical complications (e.g. chamber collapse during post-occlusion break surge).

Accordingly, one objective of the present invention is to provide a surgical console control system.

Another objective of the present invention is to provide a surgical console control system having a method for priming a surgical system.

Another objective of the present invention is to provide a more reliable method for priming a surgical system that can detect restricted irrigation flow configurations not detectable by the current methods.

These and other advantages and objectives of the present invention will become apparent from the detailed description and claims that follow.

DETAILED DESCRIPTION OF THE INVENTION

The inventors have discovered that in a balanced irrigation/aspiration ("I/A") system (inflow≧outflow) the duration of the aspiration pressure recovery to the bottle pressure (immediately following pump stop) is independent of pump run time. In fact, the pressure recovery profile has a shape that can be approximated as an exponential settling:

$$P(t) = P_{SRC} - (P_{TEST} + P_{SRC}) \cdot e^{-\frac{t}{\tau}}$$

Where: $P_{SRC}$—irrigation source pressure
$P_{TEST}$—initial system pressure after pump stop
$\tau$—time constant for a given setup Given the approximation above, the recovery time does not depend on the initial vacuum, instead it's a function of the time constant only, and is equal to $5\tau$. The time constant depends on system configuration such as infusion sleeve, diameter of the tubing, infusion set drip chamber, etc. The method of the present invention does not require the knowledge of the exact recovery time or time constant, but rather utilizes the fact that recovery time is constant. Further, in the case of an imbalanced system, fluid starvation of the test chamber during pump run time extends the recovery time because not only is the test chamber recovery being slowed down by restricted infusion, but an additional amount of time is needed to refill the previously starved test chamber. As a result, test chamber refill duration is directly proportional to pump run time. Thus, by extending run time of the pump, the effect of test chamber starvation can be amplified for a definite detection.

Figure 1:
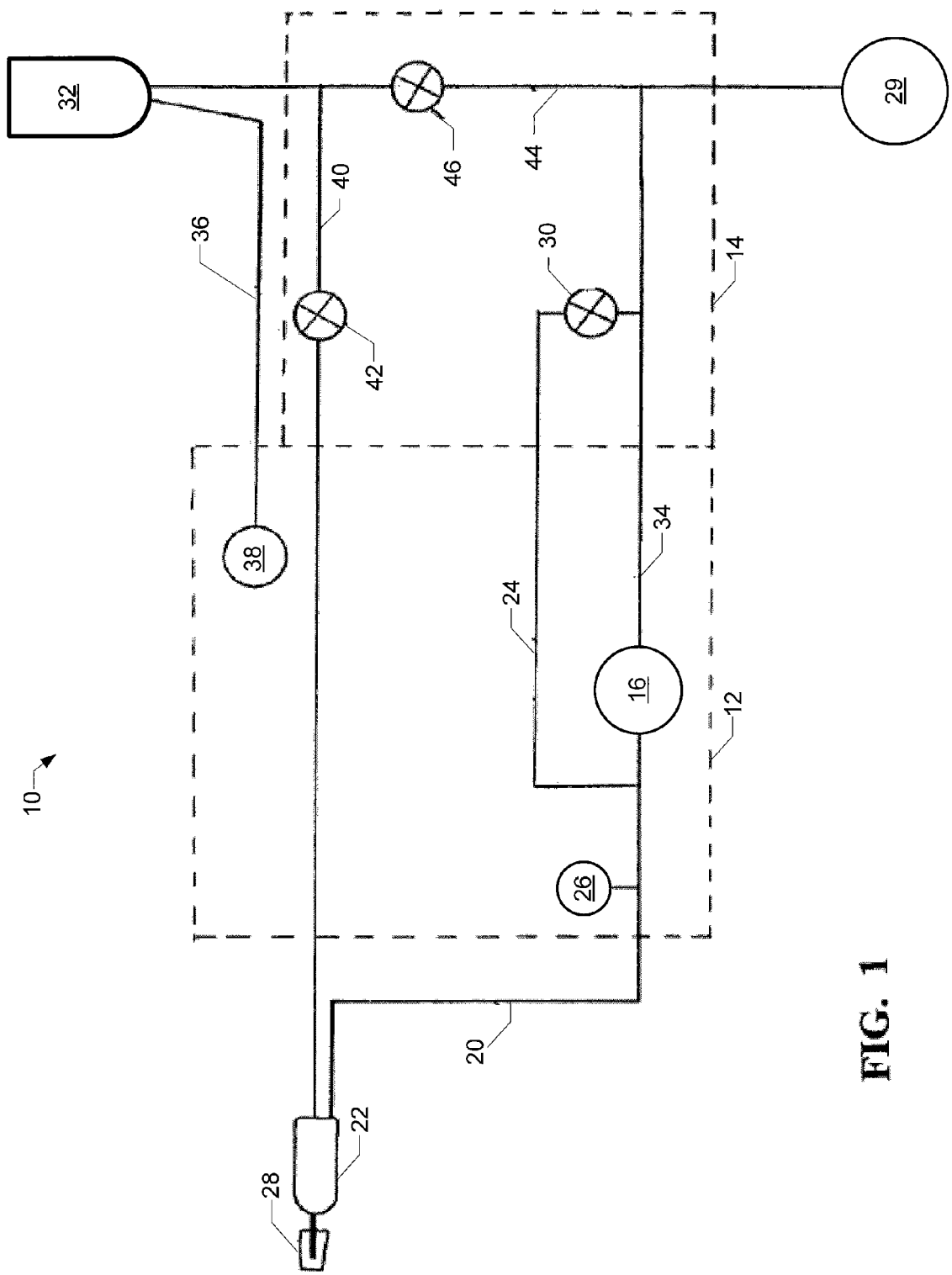
FIG. 1 is a block diagram of one embodiment of a control system that can be used with the method of the present invention.

As best seen in FIG. 1, system 10 of the present invention generally includes surgical console 12 and cassette 14. Console 12 may be any suitable commercially available surgical console, such as the SERIES TWENTY THOUSAND LEGACY®, INFINITI® or ACCURUS® surgical systems available from Alcon Laboratories, Inc., Fort Worth, Tex. Cassette 14 may be any suitable commercially available surgical cassettes, such as those described in U.S. Pat. Nos. 5,267,956, 5,364,342 and 5,499,969 (Beuchat, et al.), U.S. Pat. No. 5,899,674 (Jung, et al.), U.S. Pat. No. 6,293,926 B1 (Sorensen, et al.) and U.S. Patent Publication No. 2003/0190244 A1 (Davis, et al.), the entire contents of which being incorporated herein by reference. Cassette 14 is held in operative association with console 12 by means well-known in art.

Console 12 generally contains aspiration pump mechanism 16, which may be any suitable flow or vacuum based pump, such pumps being widely known in the art. For example, pump mechanism 16 may be a peristaltic pump roller head that interacts with a peristaltic pump tube formed by aspiration line 20 and aspiration exhaust line 34. Aspiration line 20 is connected to surgical handpiece 22 on one end and to pump mechanism 16 on the other end so as to draw fluid through handpiece 22. In fluid communication with aspiration line 20 is pressure sensor 26, which may be one of a variety of invasive or non-invasive pressure sensors well-known in the art. Aspiration line 20 is intersected between handpiece 22 and pump mechanism 16 by aspiration vent line 24.

Cassette 14 generally contains aspiration exhaust line 34, which fluidly connects to aspiration vent line 24 through vent valve 30 and to aspiration line 20 through pump mechanism 16. Aspirant or exhaust from pump mechanism 16 is directed into drain bag 29 through aspiration exhaust line 34.

System 10 of the present invention also include irrigation fluid container 32 that is connected through line 36 to pressurized air source 38. Alternatively, fluid container 32 may be gravity-fed as is well-known in the art. Fluid container 32 is fluidly connected to handpiece 22 through line 40 and valve 42 and to aspiration line 34 through irrigation vent line 44 and valve 46.

As discussed above, while it is preferred that pump mechanism 16 be a peristaltic roller head and aspiration line 20 and aspiration exhaust line 34 be formed in one continuous length so as to form a peristaltic pump tube that interacts with pump mechanism 16, one skilled in the art will recognize that aspiration line 20 and aspiration exhaust line may be formed as a separate piece or pieces or may be formed integrally with cassette 14 and that pump mechanisms 16 other that peristaltic pump roller heads may be used, such as linear peristaltic pumps.

In addition, pressure sensor 26 is depicted as being contained within console 12. One skilled in the art will recognize that portions of pressure sensor 26, such as a pressure diaphragm (not shown) may be contained in or on cassette 14 and interact with a force transducer or other means (not shown) contained within console 12.

Figure 2:
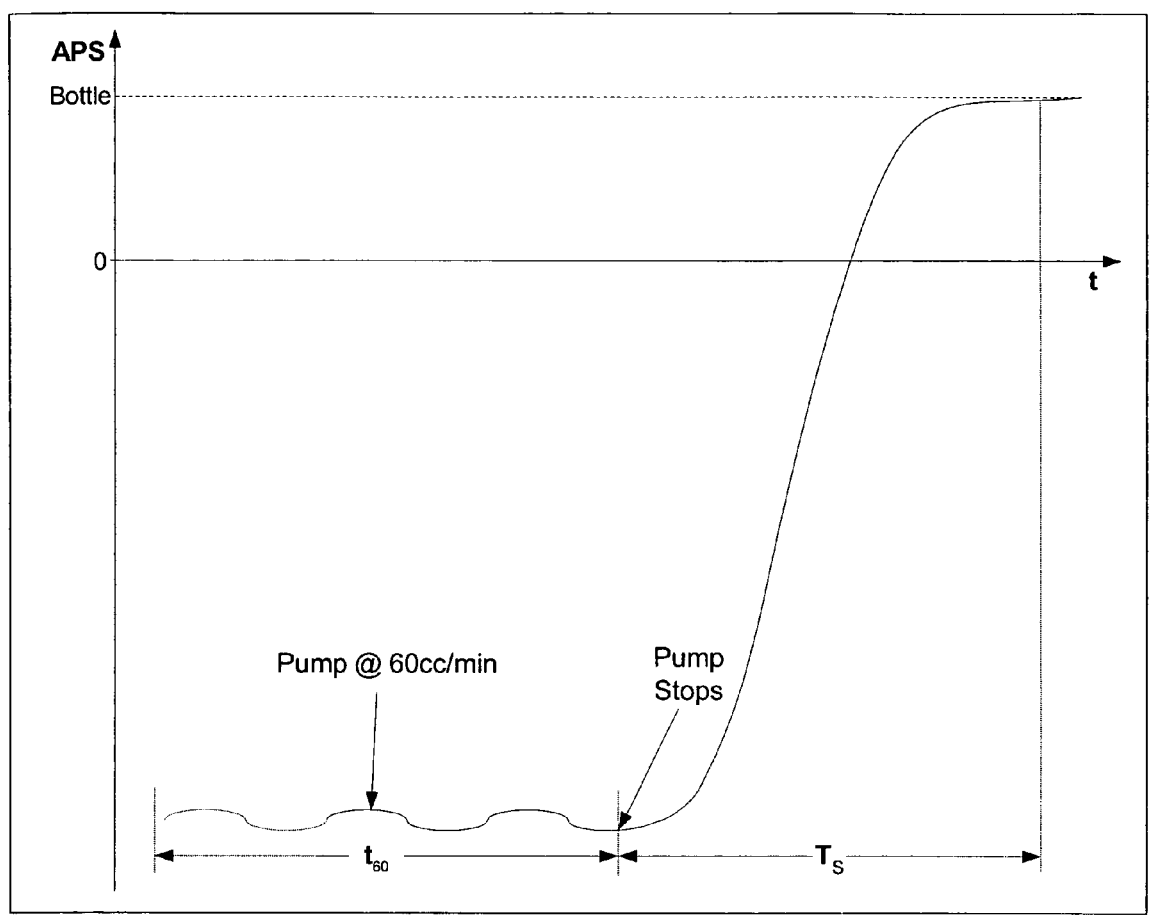
FIG. 2 is a graphical illustration of a typical aspiration pressure system waveform having unrestricted irrigation.
Figure 3:
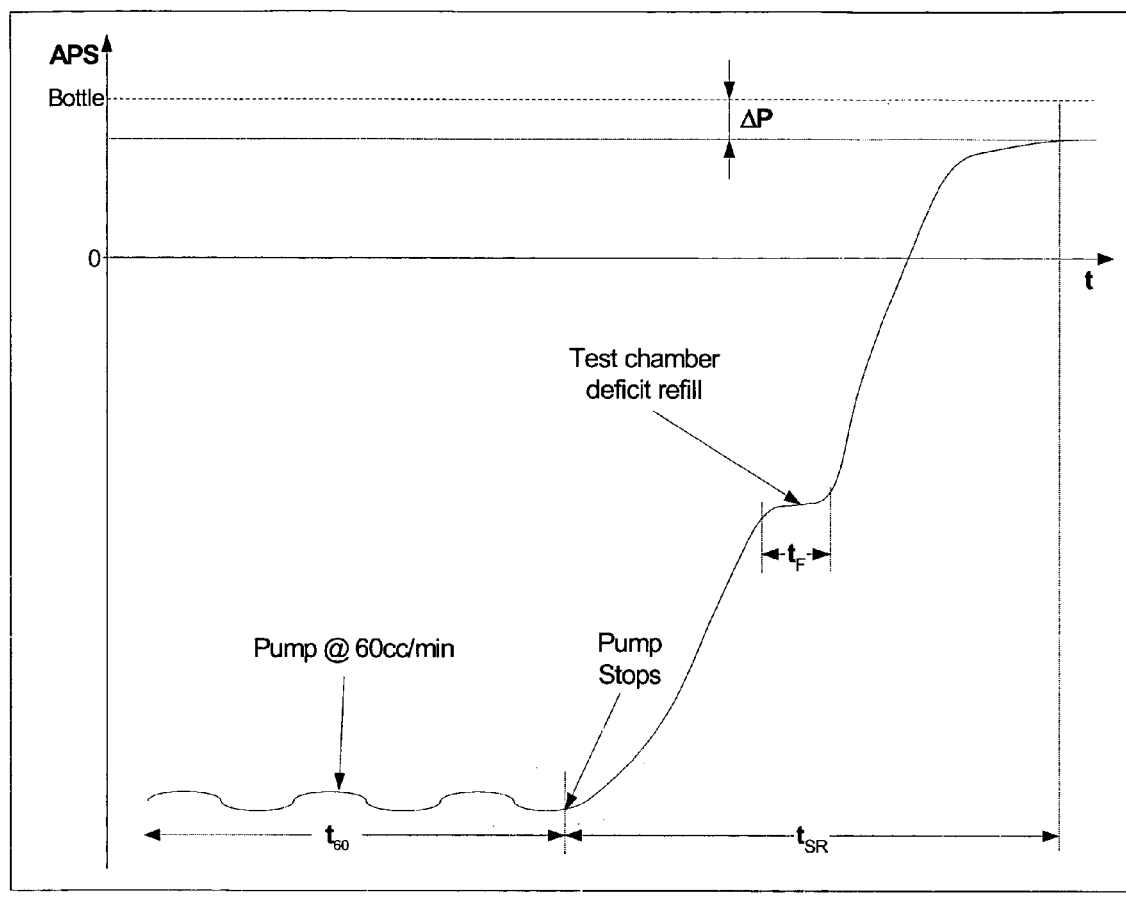
FIG. 3 is a graphical illustration of a typical aspiration pressure system waveform having restricted irrigation.
Figure 4:
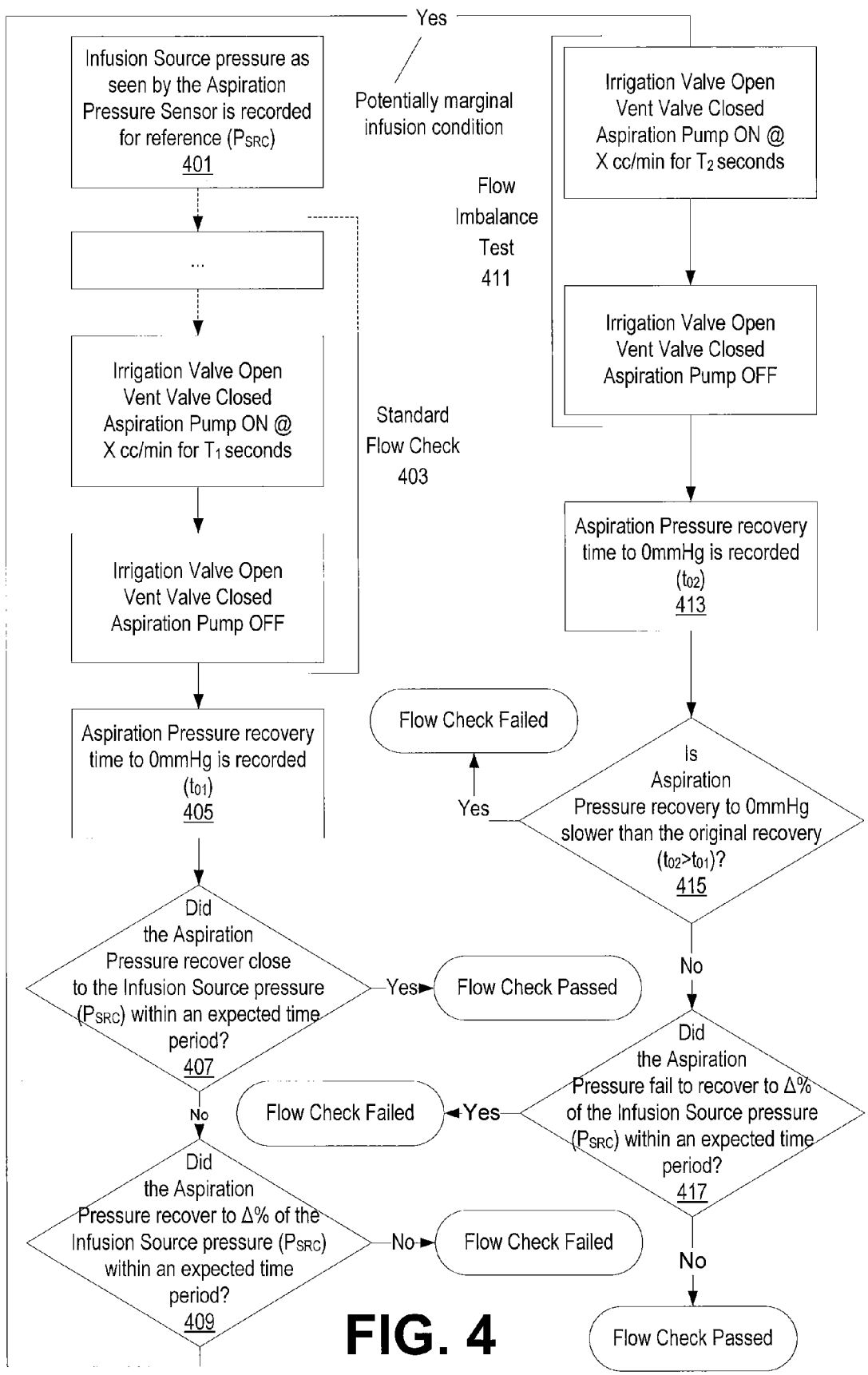
FIG. 4 is a flow chart illustrating the steps of a first embodiment of the method of the present invention.

As best seen in FIG. 2, for an I/A system, such as system 10, having unrestricted infusion, the settling time ($T_S$) of the pressure in aspiration line 20 (as indicated by aspiration pressure sensor 26 or "APS") at the end of the Flow Check cycle (pump 16 stops after running at some practical rate, for example 60 cc/min) is constant regardless of pump 16 run duration (by way of example, $t_{60}$ may be 3 seconds). For an I/A system, such as system 10, having restricted infusion, the overall settling time ($t_{SR}$) is greater than that of unrestricted system, and it can be expressed as:

$$t_{SR} = t'_S + t_F$$

where: $t'_S$—slowed down settling time ($t'_S > T_S$),
$t_F$—test chamber refill time While the slowed down settling time ($t'_S$) also remains constant for a given restriction, test chamber refill time (if applicable) depends on the degree of restriction and more importantly on pump 16 run time ($t_{60}$). The applicability of test chamber 28 refill time depends on whether test chamber 28 was starved during pump 16 run time. If, despite the restriction, the infusion fluid flow though line 40 and into test chamber 28 was able to keep up the aspiration fluid flow though line 20 caused by pump 16, then $t_F=0$. This case can be assumed as being clinically safe. The cases with a more significant restriction (i.e. when test chamber 28 is starved during pump 16 run time) present a greater risk. In these cases, test chamber 28 refill time can be estimated as follows:

$$t_F = \frac{V_{Starved}}{F_{Infusion}} = \frac{(F_{Aspiration} - F_{Infusion}) * t_{Test}}{F_{Infusion}}$$

where: $V_{Starved}$—test chamber volume lost during pump run time
$F_{Aspiration}$—aspiration flow rate during the test
$F_{Infusion}$—infusion flow rate
$t_{Test}$—pump run time, i.e. test duration As best seen in FIG. 3, for a restricted infusion flow, the overall settling time ($t_{SR}$) is greater than that of unrestricted infusion flow, and it can be expressed as:

$$t_{SR} = t'_S + t_F$$

where: $t'_S$—slowed down settling time ($t'_S > T_S$),
$t_F$—test chamber refill time Based on this information, the method of the present invention operates as shown in FIG. 4. At 401, the pressure of irrigation fluid container 32, as seen by aspiration pressure sensor 26 is recorded for future use ($P_{SRC}$). The value is measured with irrigation valve 42 open and pump 16 stopped; throughout the test, irrigation valve 42 stays open and vent valve 46 stays closed. The measured value is essentially the pressure of irrigation fluid container 32 as seen by aspiration pressure sensor 26, and it is also the recovery pressure of the aspiration pressure any time pump 16 stops. At this time, a "traditional" vacuum limit test is still used for gross error detection (e.g. aspiration side clog) provided that prior to proceeding, at 403, the test method of the present invention requires that pump 16 is run at some high rate for several seconds. For example a "high rate" may be the maximum unoccluded rate configurable by the user, such as 60 cc/min. The duration of pump 16 run time should be sufficient for the restricted irrigation flow to have some measurable effect (i.e. partial collapse of test chamber 28). The longer the duration, the higher the resolution in reliably detecting the failure; on the other hand, in the case of a non-failing setup, prolonged pump run time wastes irrigation fluid and slows down the user. Therefore, a duration that is a reasonable compromise between the two may be between 2 seconds and 6 seconds. At the end of 403, pump 16 is stopped and irrigation valve 42 stays open to allow the aspiration pressure in system 10 to recover back to the pressure in irrigation fluid container 32. At 405, the time that it takes from the point when pump 16 is stopped to the point when the aspiration pressure crosses 0 mm Hg is measured ($t_{o1}$). The value of 0 mm Hg value is chosen out of convenience, and other values may be used. The requirement for the value is that at this point, system 10 has gone through test chamber 28 recovery/refill (if any) and incurred pressure recovery delay. When test chamber 28 is being refilled the pressure at test chamber 20 is approximately 0 mm Hg and aspiration pressure reads a negative value at this point. Consequently, when aspiration pressure reads 0 mm Hg, test chamber 28 (upstream) pressure is above zero or positive, which means test chamber 28 is fully inflated. Therefore, a non-negative aspiration pressure reading is a suitable test point. Also, during 403 (pump 16 run time) the aspiration pressure reading is typically well below 0 mm Hg (i.e. vacuum) and the pressure of irrigating fluid container 32 is some positive value, and system 10 pressure necessarily has crossed 0 mm Hg at some point during recovery. At 407, after a predefined time period, the recovered aspiration pressure is compared against the expected $P_{SRS}$ value. A reasonable value for the recovery period may typically be between 0.5 to 1.5 seconds, and may be determined experimentally for the worst case combination of consumable products (cassette, tip, sleeve, etc.). The allowable differential between the actual and expected recovered values depends on sensor 26 accuracy, bottle spike, fluid level in the irrigating fluid container 26, etc; but the practical values are generally in the range of 10-15 mm Hg. If the recovered pressure is within tolerance, system 10 has passed the flow check test and no further fluidic setup is required.

At 409, if the recovered aspiration pressure failed the test at 407, then the difference in recovered value is compared against some experimentally determined threshold. A recovery above this threshold represents a marginally acceptable irrigation setup. The threshold value itself is not used to control the ability of system 10 to detect a faulty setup. Instead, this value allows system 10 to reject a bad setup sooner, without going through additional steps. Having a value that is too low makes system 10 go through extra steps before rejecting an obviously bad setup; having a value that is too high can cause false positives. A practical value may be approximately 50% of irrigating fluid container 32 pressure. The practicality of the value can be determined by simulating a worst case acceptable irrigation restriction. If the recovered aspiration pressure does pass the test at 409, indicating that the difference in recovered value as compared against some experimentally determined, threshold value is potentially acceptable, then pump 16 is restarted to repeat the last part of 403 or the "standard flow check". At 411, pump 16 run time is significantly different from the standard run time used at 403 in order to amplify the effect of the "inflow<outflow" imbalance by aggravating test chamber 28 starvation, and consequently prolonging the recovered aspiration pressure as compared against the expected $P_{SRS}$ value after stopping pump 16. By way of example, doubling pump 16 run time to 6 seconds produces a discernable difference for a faulty setup. To be able to meaningfully compare the recovery times, pump 16 rate should be set to the same value as at 403. At 413 (which may be similar to 405) a recovery period to 0 mm Hg is measured ($t_{o2}$). At 415, both recovery times ($t_{o1}$ and $t_{o2}$) are compared. A significant difference (in terms of the accuracy of the measurement) between two time indicates a longer test chamber 28 recovery/refill duration, i.e. indicates a significant "outflow>inflow" imbalance. Assuming that the overall recovery duration has two components: 1) system (tubing, cassette, etc) recovery; and 2) test chamber 28 recovery or refill, the system component is close to being a constant for any given system configuration, while test chamber 28 recovery is a variable determined by the pre-existing test chamber 28 collapse. Test chamber 28 recovery duration can be roughly approximated as the time it takes irrigation free flow to fill the deficit previously created by the outflow/inflow imbalance. Doubling pump 16 run time simplifies the math in estimating the imbalance:

$$t_{01} = t_{System} + t_{TestChamber1} = t_{System} + \frac{(F_{Aspiration} - F_{Infusoin}) * t_1}{F_{Infusoin}}$$
$$t_{02} = t_{System} + t_{TestChamber2} = t_{System} + \frac{(F_{Aspiration} - F_{Infusoin}) * 2t_1}{F_{Infusoin}}$$
$$\Rightarrow \Delta t = t_{02} - t_{01} =$$
$$\frac{(F_{Aspiration} - F_{Infusoin}) * t_1}{F_{Infusoin}} \Rightarrow \frac{F_{Infusion}}{F_{Aspiration}} = \frac{t_1}{t_1 + \Delta t}$$

Ideally, given the proper setup, Δt should be 0, and $F_{Infusion}/F_{Aspiration}$ ratio should be 1. Outside any pressure and time measurement inaccuracy, any Δt indicates some irrigation flow restriction. For example, if a flow check run at 60 cc/min for 3 and 6 seconds produces 0.5 seconds recovery differential, then $F_{Infusion}/F_{Aspiration}$ ratio can be approximated to 86%, or irrigation flow restriction of approximately 14%. Given pressure sensor 26 accuracy, time measurement accuracy, and other factors on commercially available system, approximately 15% (or a Δt of approximately 0.5 second) can be used as a practical pass/fail criteria. If the test 415 passes, then the same test as at 409 is applied for assurance that system 10 pressure recovers above a minimum threshold.

Figure 5:
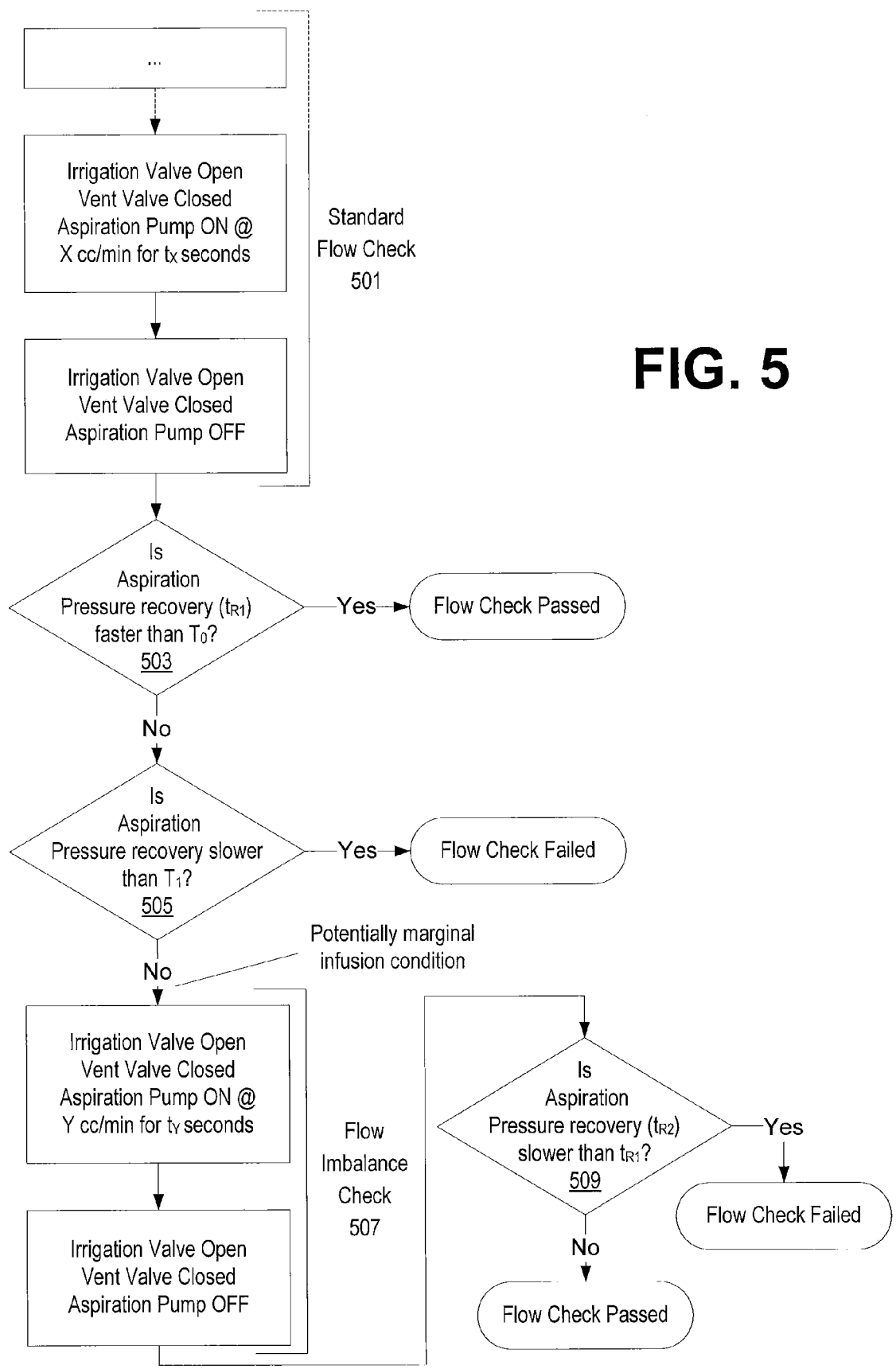
FIG. 5 is a flow chart illustrating the steps of a second embodiment of the method of the present invention.

The flow chart in FIG. 5 illustrates an alternative or second implementation of the method of the present invention. The main difference between the method illustrated in FIG. 4, and the method illustrated in FIG. 5, is that the second implementation is time based only. The method illustrated in FIG. 5 uses an expected recovery periods $T_0$ and $T_1$ as pass fail criteria in the earlier steps of the test.

One skilled in the art will recognize that the methods of the present invention are based on the principle that system 10 aspiration pressure recovery following pump 16 stop is constant for a given proper (unrestricted) setup that includes cassette, tip, irrigation sleeve, handpiece, and fluidics module. Pressure recovery in time can be approximated and an exponential approach to irrigating fluid container 32 pressure:

$$P(t) = P_{SRC} - (P_{TEST} + P_{SRC}) \cdot e^{-\frac{t}{\tau}}$$

Where: $P_{SRC}$—irrigation source pressure
$P_{TEST}$—initial system pressure after pump stop
τ—time constant for a given setup Given this approximation, the restricted setup recovery can be modeled to have similar exponential component plus a "test chamber refill" component, which is approximately linearly proportional to pump 16 run time. The fact that the exponential component of the restricted system has a greater time constant τ (i.e. slower response) than the unrestricted does not matter to the method, because a comparison of the two setups is not being made. Whatever that exponential component is, it stays constant for a given setup, so when two recoveries after two different pump run times are compared, the constant part is eliminated, thus allowing to check for the presence of the linear component.

This description is given for purposes of illustration and explanation. It will be apparent to those skilled in the relevant art that changes and modifications may be made to the invention described above without departing from its scope or spirit.

We claim:

1. A method for testing a surgical irrigation/aspiration system having an aspiration pump, comprising:
    determining a first system pressure recovery time after discontinuing aspiration of a fluid for a first time interval from a test chamber, wherein the first system pressure recovery time is a time detected for a system pressure to return to a predetermined pressure;
    determining a second system pressure recovery time after discontinuing aspiration of fluid for a second time interval from the test chamber;
    determining a dependence of the recovery time on a length of aspiration based on a comparison of the first system pressure recovery time with the second system pressure recovery time, wherein determining the dependence comprises determining if the second system pressure recovery time is greater or less than the first system pressure recovery time; and
    determining a state of the irrigation/aspiration system fluidic balance based on the determined dependency of the recovery time.

2. The method of claim 1,
    wherein the fluid is supplied to the test chamber from an irrigation fluid container;
    wherein the system pressure comprises a pressure in a fluid path between the irrigation fluid container and the aspiration pump; and
    wherein the system pressure used to determine a first or second system pressure recovery time is detected using a pressure sensor coupled to the fluid path.

3. The method of claim 1, further comprising:
    comparing the first system pressure recovery time to a first threshold, wherein if the first system pressure recovery time is greater than the first threshold, the state of the irrigation/aspiration system fluidic balance is determined to be unacceptably restricted.

4. The method of claim 1:
    wherein the state of the irrigation/aspiration system fluidic balance corresponds to at least one of two states including:
    a) a balanced irrigation/aspiration system in which a duration of the aspiration pressure recovery to an irrigation fluid source pressure following aspiration pump stop is substantially independent of pump run time; or
    b) a restricted irrigation flow configuration.

5. The method of claim 4, wherein, if the second time interval of aspiration is greater than the first time interval of aspiration, state a) is indicated by the second system pressure recovery time being less than or equal to the first system pressure recovery time.

6. The method of claim 4, wherein, if the second time interval of aspiration is greater than the first time interval of aspiration, state b) is indicated by the second system pressure recovery time being greater than the first system pressure recovery time.

7. A method for testing a surgical irrigation/aspiration system having an aspiration pump, comprising:
    monitoring a system pressure recovery profile after discontinuing aspiration of a fluid from a test chamber;
    determining a presence or absence of a characteristic test chamber refill response in the recovery profile; and
    determining a state of an irrigation/aspiration system fluidic balance based on the determined presence or absence of the chamber refill response;
    wherein the fluid is supplied to the test chamber from an irrigation fluid container; and wherein the system pressure comprises a pressure in a fluid path between the irrigation fluid container and the aspiration pump.

8. The method of claim 7,
wherein a pressure for the system pressure recovery profile is detected using a pressure sensor coupled to the fluid path; and
wherein a pressure of the irrigation fluid container, as detected through the fluid path by the pressure sensor, is recorded prior to starting aspiration of the fluid.

9. The method of claim 7, wherein aspiration of the fluid from the test chamber comprises aspirating fluid from the test chamber through the aspiration pump for a predetermined time interval.

10. The method of claim 7, wherein the state of the irrigation/aspiration system fluidic balance corresponds to at least one of two states including:
a) a balanced irrigation/aspiration system in which a duration of the aspiration pressure recovery to an irrigation fluid source pressure following aspiration pump stop is substantially independent of pump run time; or
b) a restricted irrigation flow configuration;
wherein state b) is indicated by the presence of the characteristic test chamber refill response in the recovery profile and wherein state a) is indicated by the absence of the characteristic test chamber refill response in the recovery profile.

11. The method of claim 10, wherein in the balanced irrigation/aspiration system state, the pressure recovery profile corresponds to:

pressure(time) = Irrigation source pressure −

(Initial system pressure after aspiration pump stop + irrigation source pressure)$^* e^{-\frac{time}{time\_const}}$ where time_const is dependent on system configuration.

12. The method of claim 10, wherein in the restricted irrigation flow configuration, a test chamber refill time, after the aspiration pump discontinues, is substantially proportional to aspiration pump run time.

13. The method of claim 7, wherein the fluid is aspirated from the test chamber for a first time and wherein the method further comprises:
aspirating the fluid from the test chamber for a second time;
monitoring the system pressure recovery profile following aspiration of the fluid from the test chamber for the second time; and
determining a presence or absence of a characteristic test chamber refill response in the system pressure recovery profile following the aspiration of the fluid from the test chamber for the second time.

14. The method of claim 13,
wherein the system pressure recovery profile includes at least one system pressure detected at a known time period after the aspiration of the fluid from the test chamber for the second time;
wherein determining the absence of the characteristic test chamber refill response in the recovery profile comprises determining that the system pressure detected at the known time period is approximately an expected system pressure or at least a predetermined percentage of the expected system pressure; and
wherein determining the presence of the characteristic test chamber refill response in the recovery profile comprises determining that a system pressure detected at the known time period is not at least a predetermined percentage of an expected system pressure.

15. The method of claim 13, further comprising:
determining a time ($t_{o1}$) for the system pressure to return to a pressure ($P_1$) after aspirating the fluid from the test chamber for the first time; and
determining a time ($t_{o2}$) for the system pressure to return to $P_1$ after aspirating the fluid from the test chamber for the second time;
wherein determining the absence of the characteristic test chamber refill response in the recovery profile comprises determining that $t_{o2}$ is less than or equal to $t_{o1}$.

16. A method for testing a surgical irrigation/aspiration system having an aspiration pump, comprising:
monitoring a system pressure recovery profile after discontinuing aspiration of a fluid from a test chamber;
determining a presence or absence of a characteristic test chamber refill response in the recovery profile; and
determining a state of an irrigation/aspiration system fluidic balance based on the determined presence or absence of the chamber refill response;
wherein the system pressure recovery profile includes at least one system pressure detected at a known time period after the aspiration of the fluid from the test chamber.

17. The method of claim 16, wherein determining the absence of the characteristic test chamber refill response in the recovery profile comprises determining that a system pressure detected at the known time period is approximately an expected system pressure or at least a predetermined percentage of the expected system pressure.

18. The method of claim 16, wherein determining the presence of the characteristic test chamber refill response in the recovery profile comprises determining that a system pressure detected at the known time period is not at least a predetermined percentage of an expected system pressure.

19. The method of claim 18,
wherein the predetermined percentage is approximately 50%;
wherein the expected system pressure is a pressure of the irrigation fluid container; and
wherein the presence of the characteristic test chamber refill response in the recovery profile comprises the system pressure detected at the known time period not being at least approximately 50% of the pressure of the irrigation fluid container.

* * * * *

UNITED STATES PATENT AND TRADEMARK OFFICE
CERTIFICATE OF CORRECTION

PATENT NO. : 7,644,603 B2 Page 1 of 1
APPLICATION NO. : 11/167646
DATED : January 12, 2010
INVENTOR(S) : Gordon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1206 days.

Signed and Sealed this

Sixteenth Day of November, 2010

David J. Kappos
*Director of the United States Patent and Trademark Office*